United States Patent
Hansen et al.

(12)

(10) Patent No.: US 6,433,560 B1
(45) Date of Patent: Aug. 13, 2002

(54) COMBINED FLUID CONDITION MONITOR AND FLUID LEVEL SENSOR

(75) Inventors: James E. Hansen, Franklin; Edward F. Buck, Waldo; Lian Q. Zou, Shorewood; Victor E. Shtaida, Franklin; Peter J. McGinnis, Brookfield; Birger Pahl, Milwaukee, all of WI (US)

(73) Assignee: Eaton Corporation, Cleveland, OH (US)

( * ) Notice: Subject to any disclaimer, the term of this patent is extended or adjusted under 35 U.S.C. 154(b) by 0 days.

(21) Appl. No.: 09/944,897

(22) Filed: Aug. 31, 2001

(51) Int. Cl.[7] .......................... G01R 27/26; G01N 27/02

(52) U.S. Cl. ........................................ 324/668; 324/441

(58) Field of Search ................................. 324/441, 668, 324/439, 442, 444

(56) References Cited

U.S. PATENT DOCUMENTS 6,278,281 B1 * 8/2001 Bauer et al. .................. 324/441

\* cited by examiner

*Primary Examiner*—N. Le
*Assistant Examiner*—James Kerveros
(74) *Attorney, Agent, or Firm*—Roger A. Johnston

(57) ABSTRACT

A combination fluid condition monitor and fluid level sensor having an excitation electrode divided into two segments disposed closely spaced and parallel to current sensing electrode. For the fluid condition monitoring mode function both segments of the excitation electrode are commonly excited sequentially at high and low frequencies and the currents sensed in the sensing electrode employed to compute the difference in impedance for determining the fluid condition. For the level sensing mode function a mode switching circuit grounds one of the excitation electrode segments and excites the other then grounds the other segment and excites the one segment and the resultant currents ratioed to determine the amount of electrode immersed in fluid and hence the fluid level.

10 Claims, 5 Drawing Sheets

COMBINED FLUID CONDITION MONITOR AND FLUID LEVEL SENSOR

BACKGROUND OF THE INVENTION

The present invention relates to transducers of the type employed for providing a continuous electrical indication in real time of the chemical/contaminate condition of a fluid such as hydraulic fluids and for additive depletion, acidity and other types of degradation of lubricants employed in internal combustion engines and power transmission devices. An example of such a device employing impedance spectroscopy techniques for fluid monitoring is that shown and described in co-pending application Ser. No. 220,556, filed Dec. 23, 1998 entitled "Fluid Condition Monitor", now U.S. Pat. No. 6,278,281, and assigned to the Assignee of the present application. The aforesaid device utilizes a probe having interdigitated elements immersed in the fluid and excited by an alternating current signal sequentially at a low frequency and at a higher frequency. The resulting voltage is measured during excitation at both frequencies and the impedance is computed and the difference in impedance between the high and low frequency utilized as an indication of the fluid condition which can be determined from a look-up table of differential impedance measurements taken of fluids having a known condition. The sensing device or transducer has heretofore employed a probe having a pair of electrodes disposed in closely spaced generally parallel arrangement and immersed in the fluid with electrical connections made thereto such that one electrode is excited by the alternating voltage sequentially at the selected frequencies; and, the sensed or output current from which the impedance determinations are made flows through and is detected in the remaining electrode.

Referring to FIG. 6, a known system for determining fluid conditions such as that described in co-pending application Ser. No. 220,556, filed Dec. 23, 1998 entitled "Fluid Condition Monitor" in the names of R. A. Bauer et al. and assigned to the Assignee of the present invention is illustrated. The known system of FIG. 6 employs the technique of sequentially exciting a probe having a pair of electrodes immersed in the fluid with alternating excitation voltage at low and high frequencies such as 0.01 hertz and 10 hertz respectively and determining the resultant current flow in the other electrode and computing the difference in impedance arrived from the measured currents. The system as indicated generally at 1 in FIG. 6 and employs an excitation electrode 2 immersed in the fluid to be monitored with a current sensing or output electrode 3 disposed in closely spaced generally parallel interdigitated arrangement. The electrode 2 receives excitation voltage through a shielded lead 4 which receives an analog excitation signal from an electronic controller (not shown in FIG. 6) applied through a level shifter 5. The output or current sensing electrode 3 is connected via a shielded lead 6 of the input of a current to voltage converter 7 the output of which is applied through a level shifter 8 connected to the input of an analog to digital converter provided in the unshown electronic controller. The current to voltage converter 7 has a variable resistor $R_F$ which is varied by an auto range control signal received from the unshown controller along 9. The signal processing for the system is sufficiently shown and described in the aforesaid co-pending application and the details thereof are incorporated herein by reference and not repeated for the sake of brevity.

A separate set of level sensing electrodes 12, 13 is immersed in the fluid and connected by leads 14, 15 to the unknown controller. The prior art system of FIG. 6 includes a separate temperature sensing device such as a thermistor denoted by reference numeral 10 immersed in the fluid and which provides a signal through line 11 to temperature sensing signal processing circuitry provided in the unshown electronic controller.

It is also known to provide the prior art system of FIG. 6 with an alternative configuration for the arrangement of the probe electrodes in the form of a spiral or helically disposed spaced parallel wires in place of the interdigitated electrodes 2, 3 as shown in FIG. 6. Such a helical configuration for the probe is shown and described in co-pending application 09/432,971, filed Nov. 3, 1999 entitled "Monitoring Fluid Condition With A Spiral Electrode Configuration" and filed in the names of M. H. Polcyznsky et al. and assigned to the Assignee of the present invention.

Heretofore, where it was also desired to provide an electrical indication of the fluid level in the reservoir or vessel for which the condition sensor or monitor was being employed, it has been necessary to provide an additional electrode set in the fluid and to provide support therefore in spaced relationship to the fluid condition sensing electrodes and to provide separate electronic circuitry for electrically determining the fluid level. This arrangement has proven relatively costly and has complicated the construction of the fluid condition monitoring probe assembly and installation of same, particularly where the fluid to be monitored is contained in a reservoir or vessel which is required to be sealed.

In particular where it is desired to employ the fluid condition monitoring sensor on board a motor vehicle for providing a continuous electrical indication of the condition of the fluid in either the transmission or the engine oil sump, the complications of adding an additional electrode for fluid level sensing have been considered prohibitive in high volume mass production from a cost and complexity of installation standpoint. Accordingly, it has long been desired to provide a way or means of sensing the fluid level in the reservoir vessel for which a fluid condition monitor is employed and to provide an electrical indication of the fluid condition without the need for separate fluid level sensing electrodes.

BRIEF SUMMARY OF THE INVENTION

The present invention solves the above described problem of providing a combined fluid condition sensing function with fluid level sensing in a common sensor probe without the need for a separate electrode and circuitry for the sensing function. The sensor of the present invention utilizes a pair of closely spaced generally parallel electrodes immersed in the fluid with one of the electrodes divided into an upper and lower section which are electrically connected together and commonly excited by an alternating current sequentially at a high and low frequency for determining the fluid condition. The remaining electrode is the sensing electrode and provides a signal current to the electronic controller for computation of the differential impedance at the high and low frequencies of excitation for determination of the fluid condition from stored information.

For the level sensing function the excitation electrode is divided into upper and lower sections which are excited separately; and, the ratio of the currents and signal phase shifts determined from excitation of each section provides an indication of whether both electrodes are immersed in fluid, e.g., that the fluid is at the desired level. If either electrode is above the fluid level a significant increase in phase shaft is detected. The ratio of the current may be used to indicate the proportion of the electrodes immersed to thereby determine intermediate levels of the fluid. The present invention thus combines fluid level sensing with fluid condition monitoring in the same probe by segmenting the excitation electrode and eliminates the need for providing a separate set of electrodes for the level sensing function.

DETAILED DESCRIPTION OF THE INVENTION

Figure 1:
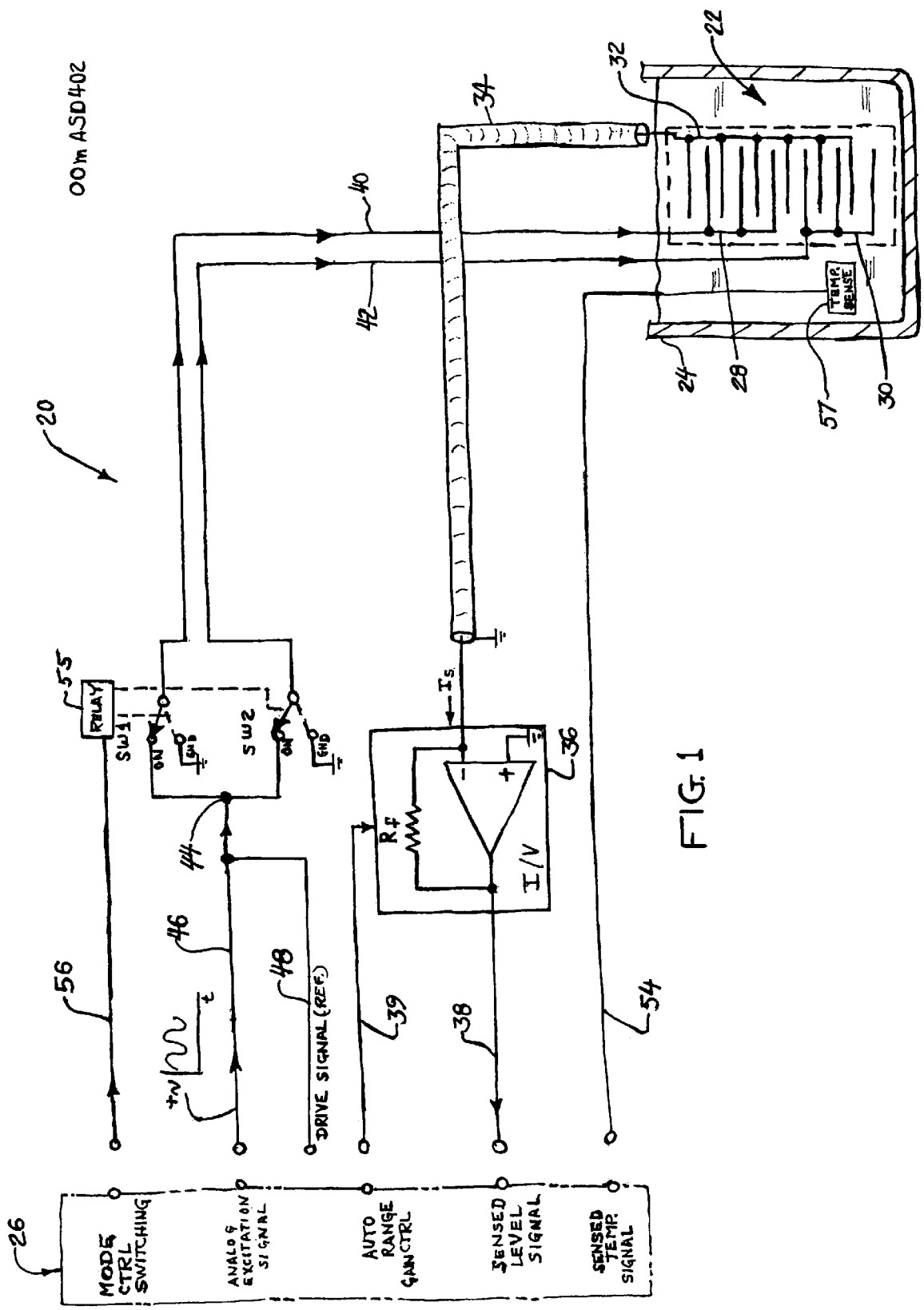
FIG. 1 is a pictorial schematic of the combined level sensing and fluid monitoring system of the present invention.
Figure 2:
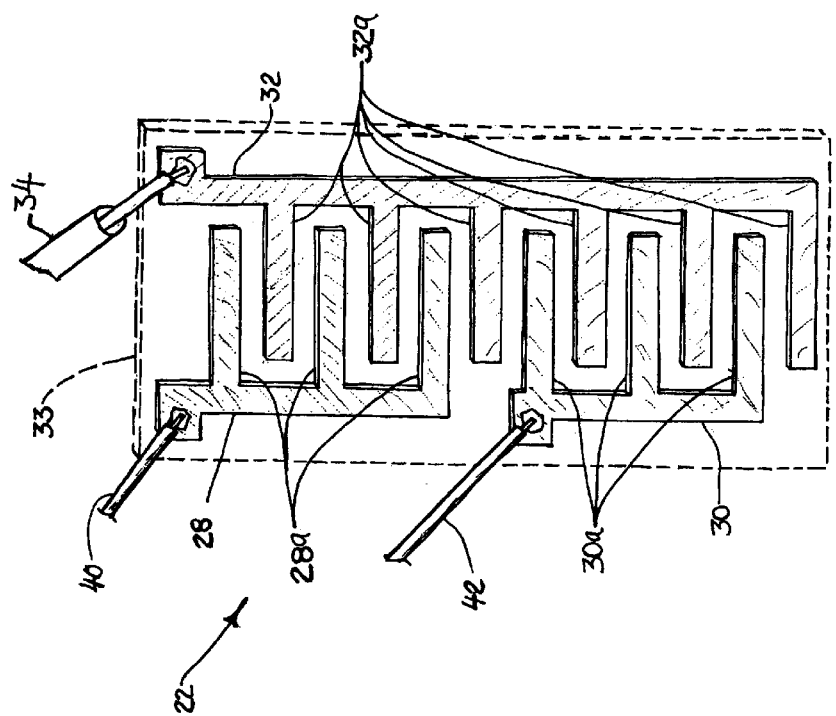
FIG. 2 is a pictorial view of a sensing probe in a planar array for the system of FIG. 1.
Figure 3:
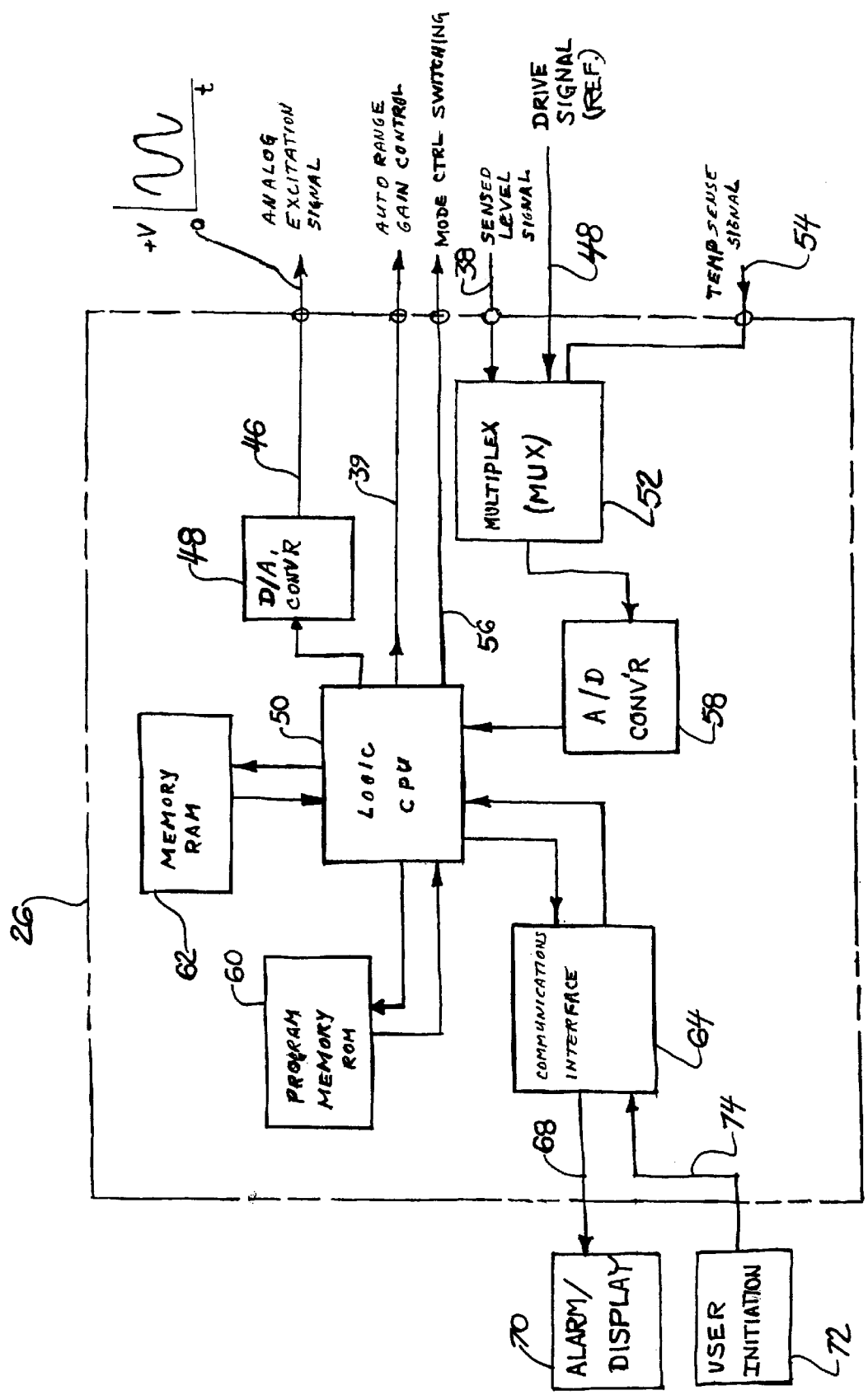
FIG. 3 is a block diagram of the electronic controller functions for the system of FIG. 1.

Referring to FIGS. 1–3, the system of the present invention as indicated generally at 20 and includes a sensor probe indicated generally at 22 which is immersed in a liquid to be monitored contained in the vessel or reservoir 24. Although the reservoir is shown open in FIG. 1, it will be understood that in certain applications, the reservoir may be closed or sealed. The system of the present invention is connected to an electronic controller indicated generally at 26 which contains the signal processing circuitry for the fluid condition monitoring function, which circuitry is shown and described in the aforesaid co-pending applications and is omitted herein for the sake of brevity.

The probe 22 is shown in enlarged detail in FIG. 2 and includes excitation electrodes 28, 30 comprising a lower excitation electrode 30 and an upper excitation electrode 28 disposed preferably in alignment and closely spaced parallel arrangement with a pick up or current sensing electrode 32. The electrodes each have interdigitated fingers denoted respectively 28a, 30a, and 32A. The current sensing electrode 32 is connected to a shielded lead 34 which provides a sensed current signal to the negative input of a current to voltage converter 36 which has a feedback resistor $R_f$ with the output of the converter 36, connected along line 38 to the sensed level signal input of the controller 26.

The excitation electrodes 28, 30, 42 are respectively connected by leads 40, 42 to the common side of single pole double throw mode control switches SW1, SW2.

The feedback resistor $R_f$ is varied by an auto range control signal from the controller 26 applied along line 39 to enable the probe to accommodate the range of current sensed by the probe in fluids of varying impedances.

The probe 22 may either be free standing or with the interdigitated members formed of sufficient thickness to maintain a planar array as shown in FIG. 2 in solid outline. Alternatively the electrodes 28, 30, 32 may be of film deposited on a substrate indicated in dashed outline in FIG. 2 and denoted by reference numeral 33.

The mode control switches SW1, SW2 each have the "ON" side terminal thereof connected to a common input junction 44 which receives an analog excitation signal along line 46 from the controller 26. The analog excitation signal from controller 26 is generated by the D to A converter 48 which receives inputs from the logic central processing unit 50 of the controller 26, which contains the circuitry for generating the excitation signals for both the fluid condition monitoring function and the level sense function. The logic CPU 50 also provides an auto range gain control signal to line 39.

Referring to FIGS. 1 and 3, a drive signal reference is provided from junction 44 to a reference input of a Multiplexer 52 provided in the controller 26. The level sense signal along line 38 is also applied to a separate input of the Multiplexer 52. The multiplexer 52 also receives an input of the sensed temperature along line 54 from a temperature sensor 56 immersed in the fluid adjacent the probe 22.

The side terminals of SW1, SW2 opposite the "ON" terminals are each respectively grounded as shown in FIG. 1. The common switching terminals of SW1, SW2 are respectively controlled through a relay 55 by a Mode Control Switching signal output from the Logic CPU 50 along line 56 as shown in FIG. 1. It will be understood that the switches SW1, SW2 are illustrated as a mechanical switches in FIG. 1 for purposes of functional illustration; however, the switching functions of SW1, SW2 are preferably performed electronically and may be incorporated in the controller if desired.

The Multiplexer 52 provides an output to an A to D Converter 58 which provides inputs to the logic CPU 50. The logic CPU 50 is also connected to program memory ROM 60 and memory RAM 62 within the controller 26. Logic CPU 50 is also connected to a communications interface 64 which provides outputs along line 66 to an Alarm/Display 70 which is preferably remotely located from the controller 26. A User Initiation signal 72 is provided along line 74 to an input of the Communications Interface 64.

Figure 4:
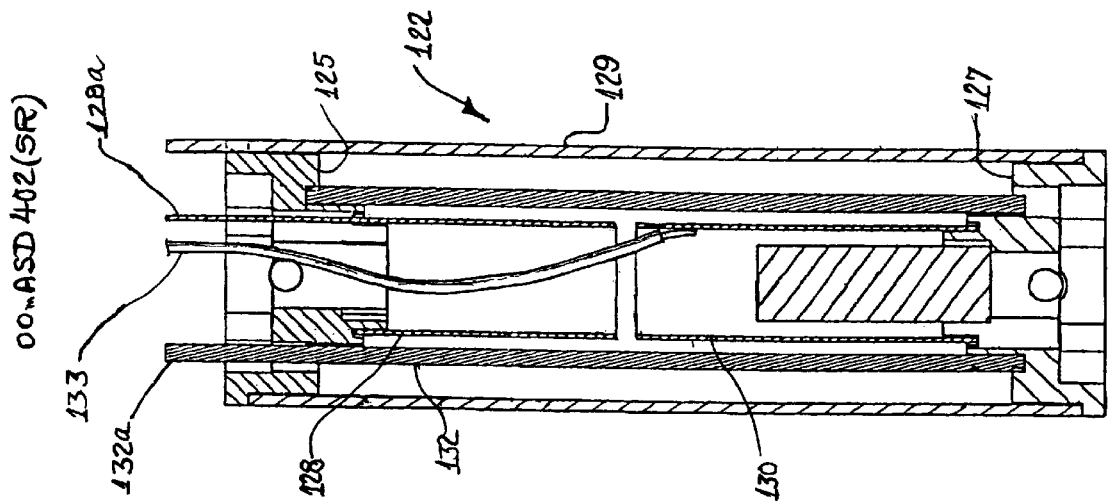
FIG. 4 is a cross section of an alternate embodiment of the sensing probe for the system FIG. 1.

Referring to FIG. 4, an alternate embodiment of the probe is indicated generally at 122 and include an upper excitation electrode 128 having a tubular configuration and mounted on a block 125 within an outer cylindrical tubular casing 129. A lower excitation electrode in the form of tube 130 mounted on a lower block 127 and extending upwardly therefrom within casing 129 in aligned spaced relationship with the upper excitation electrode 132.

The current sensing electrode 132 has a tubular configuration and surrounds electrodes 128,130. Sensing electrode 132 has a portion 132a extending upwardly through block 125 for electrical connection thereto by the shielded lead 34.

Lower excitation electrode 130 has a lead 133 connected thereto which extends upwardly through block 125 for connection to lead 42. Similarly, the upper excitation electrode 128 has a portion 128a thereof extending upwardly through block 125 and is connected to lead 40. The probe 122 of FIG. 4 thus has a coaxial arrangement of the excitation and sensing electrodes.

Figure 5:
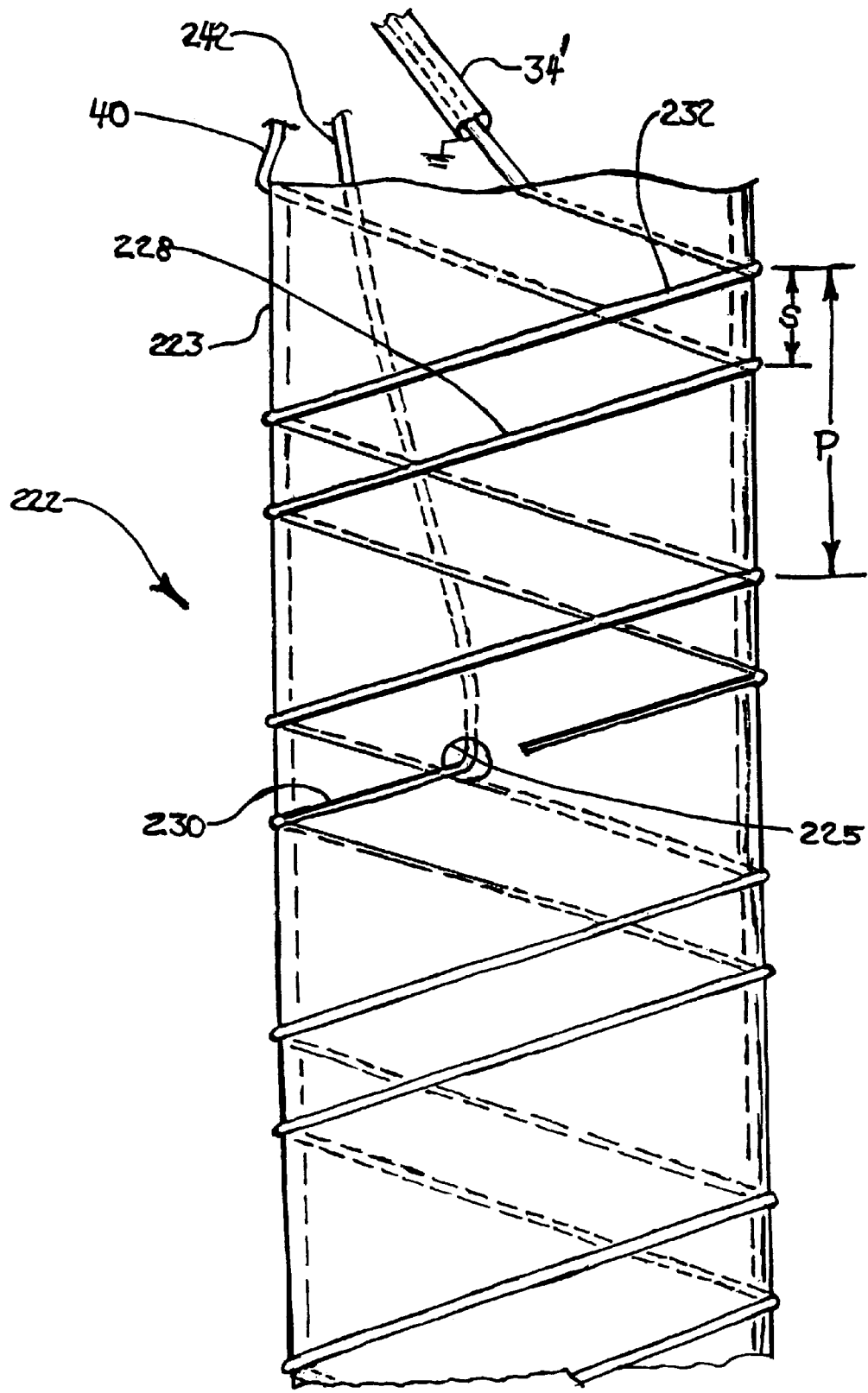
FIG. 5 is a cross sectional view of another embodiment of the sensing probe for the system of FIG. 1.
Figure 6:
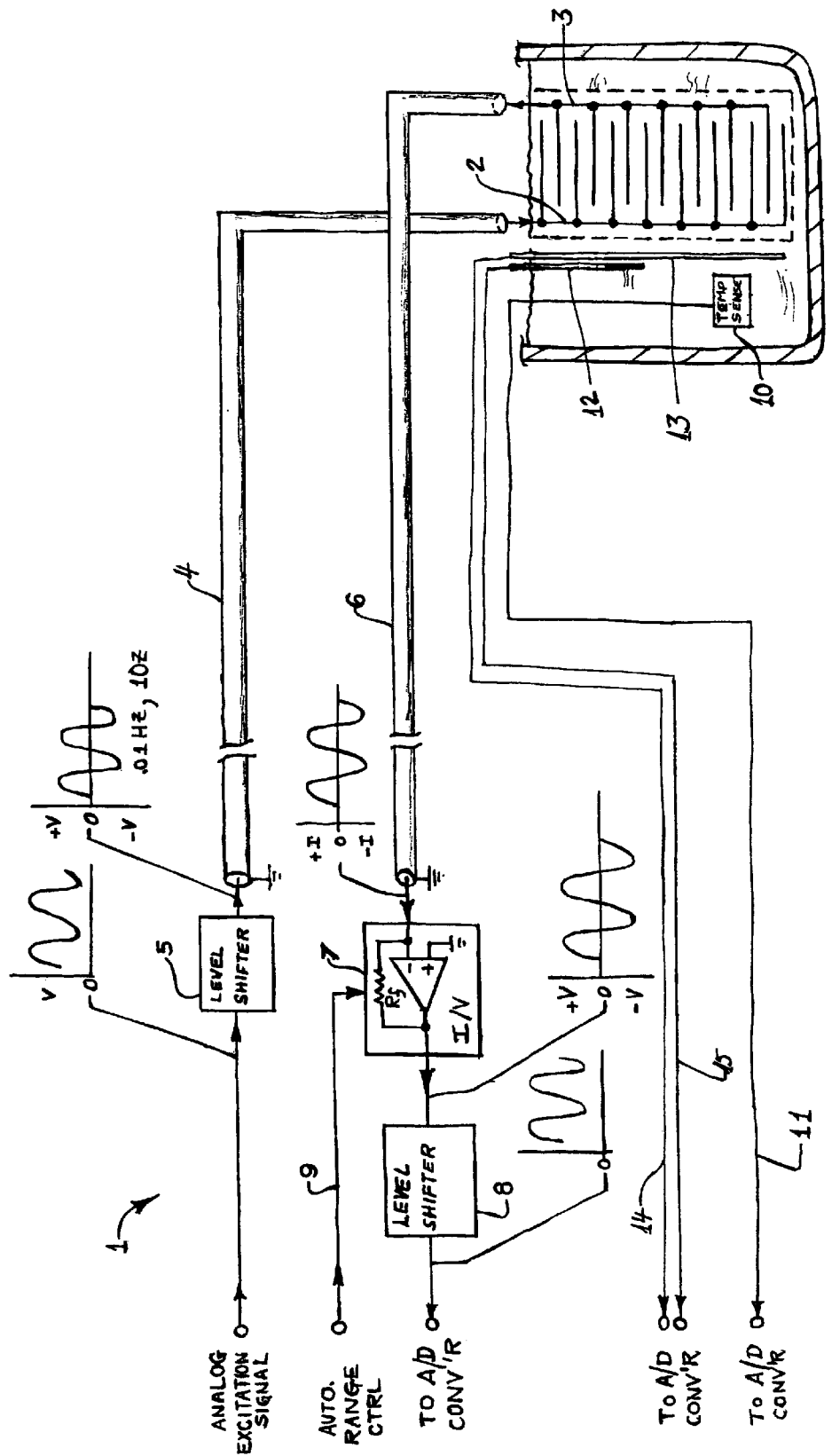
FIG. 6 is a schematic of a prior art fluid monitoring system.

Referring to FIG. 5, another embodiment of the probe located generally at 222 is illustrated as having the electrodes disposed on a hollow tubular support 223 which it will be understood it is immersed in the liquid within the vessel 24.

The probe 222 has a current sensing electrode in the form of a wire 232 helically wound on support 223 at a pitch denoted by the dimension "P" in FIG. 5 which extends downwardly the length of support 223. An upper excitation electrode in the form of wire 228 is wound on support 223 at a corresponding pitch "P" and spaced from wire 232 a uniform distance denoted by the reference "S" in FIG. 5; and, wire 228 extends downwardly by a distance approximately to the midpoint of the sensing electrode 232 and the wire 228 is terminated thereupon. A lower excitation electrode in the form of wire 230 is also helically wound on support 223 at the pitch "P" and in spaced relationship to the sensing electrode 228 by a distance "S" and extends downwardly by a distance to the lower end of the sensing electrode 232.

The upper excitation electrode 228 is connected at its upper end to lead 40; and, the lower excitation electrode 230 is connected a lead 242 which extends through an aperture 225 provided in the support 223 and upwardly through support tube 223. The sensing electrode 232 is connected at its upper end to the shielded lead 34' which it will be understood is connected to the Current to Voltage Converter 36.

In operation, the switches SW1, SW2 are moved to the position shown in solid outline in FIG. 1 with the common connectors of each to the "ON" side terminal for the fluid condition monitoring mode of operation.

For the fluid level sensing function mode of operation, switch SW1 is moved by the remote Mode Control Switching signal to the position shown in dashed outline in FIG. 1 to the grounded side terminal. The excitation current is applied through switch SW2 to the lower electrode 30 and the sensed current in electrode 32 is determined by Controller 26. The remote Mode Control Switching signal then returns switch SW1 to the "ON" position and moves switch SW2 to the grounded position; and, electrode 28 is then excited through switch SW1 and the sensed current determined in electrode 32. The Logic CPU then determines the ratio of the currents sensed by the individual excitation of electrodes 28, 30. The ratio is employed to determine the proportion of the electrodes immersed in the fluid with reference to a 1:1 ratio of the currents representative of the liquid level completing filling the reservoir.

In the event that the fuel level is below both electrodes, the resultant currents are below a predetermined threshold, and the system interprets this as a fault. In addition, the phase shift is increased.

The present invention thus provides a unique and novel fluid condition monitoring probe which has the excitation electrode divided at its midpoint and permits alternate excitation of the upper and lower portions of the electrode; and, the ratio of sensed currents is employed to determine the proportion of the electrodes immersed in the fluid to thereby determine fluid level. The fluid monitoring function is performed by common excitation of the upper and lower electrode portions of the excitation electrode together thereby utilizing the same electrode arrangement for both functions.

Although the invention has hereinabove been described with respect to the illustrated embodiments, it will be understood that the invention is capable of modification and variation and is limited only by the following claims.

What is claimed is:

1. A method for sensing condition and level of a fluid in a reservoir comprising:
    (a) disposing a first electrode at least partially in the fluid;
    (b) disposing a second electrode in the fluid closely spaced adjacent an upper portion of said first electrode;
    (c) disposing a third electrode in the fluid closely spaced adjacent a lower portion of said first electrode;
    (d) grounding said third electrode and exciting said second electrode with an alternating voltage and sequentially grounding said second electrode and exciting said third electrode with and alternating voltage and detecting the current in said first electrode from said excitations;
    (e) comparing the detected currents and determining therefrom the fluid level in the reservoir; and
    (f) exciting said second and third electrodes simultaneously with a relatively low frequency alternating voltage and detecting the current in said first electrode and determining the bulk and surface impedances and determining from known relationship of condition versus impedance the condition of the fluid.

2. The method described in claim 1, wherein said steps of disposing said second electrode includes interdigitating said second electrode with the upper portion of said first electrode and the step of disposing said third electrode includes interdigitating said third electrode with said lower portion of said first electrode.

3. The method described in claim 1, wherein the steps of disposing said first, second and third electrodes in the fluid includes mounting said electrodes on a substrate.

4. The method defined in claim 1, wherein said steps of disposing said second and third electrodes includes equalizing the length of said first and second electrodes.

5. The method defined in claim 1, wherein said step of detecting the current in said first electrode includes converting the current to a voltage.

6. The method defined in claim 1, wherein said step of detecting the current in said first electrode includes connecting a shielded lead to said first electrode.

7. The method defined in claim 6, wherein said step of detecting the current from said first electrode includes connecting said shielded lead to a current-to-voltage converter.

8. The method defined in claim 1, wherein said step of detecting the current from each of the excitations includes rationing the currents detected from excitation of said second and third electrodes.

9. The method defined in claim 1, wherein said step of disposing a first, second and third electrode include disposing said first, second and third electrodes in helical arrangement.

10. The method as defined in claim 1, wherein said steps of disposing said second and third electrodes includes disposing the second and third electrodes co-axially about said first electrode.

* * * * *